United States Patent [19]

Böhshar et al.

[11] Patent Number: 5,075,485
[45] Date of Patent: Dec. 24, 1991

[54] PROCESS FOR THE PREPARATION OF N-ACYLPHOSPHINOTHRICIN DIESTERS

[75] Inventors: Manfred Böhshar, Kelkheim; Heinz Erpenbach, Cologne; Erhard Jägers, Bornheim; Hanss-Jerg Kleiner, Kronberg; Hans-Peter Koll, Hürth, all of Fed. Rep. of Germany

[73] Assignee: Hoechst Aktiengesellschaft, Frankfurt am Main, Fed. Rep. of Germany

[21] Appl. No.: 373,330

[22] Filed: Jun. 29, 1989

[30] Foreign Application Priority Data

Jul. 14, 1988 [DE] Fed. Rep. of Germany ....... 3823885
Apr. 27, 1989 [DE] Fed. Rep. of Germany ....... 3913891

[51] Int. Cl.$^5$ .................................................. C07F 9/30
[52] U.S. Cl. ...................................................... 558/87
[58] Field of Search ......................................... 558/87

[56] References Cited

U.S. PATENT DOCUMENTS 3,974,243  8/1976  Kleiner .................... 558/87
4,264,532  4/1981  Tsuruoka et al. ........ 260/968
4,906,764  3/1990  Takamatsu ............... 558/87

FOREIGN PATENT DOCUMENTS 0018415  11/1980  European Pat. Off. .
0292918  11/1988  European Pat. Off. .

OTHER PUBLICATIONS

A guidebook to mechanism in Organic Chemistry by P. Syken, p. 210.
Chemical Abstracts, vol. 104, 1986, No. 33873F.
H. Wakamatsu, *Chemical Communications*, p. 1540 (1971).

*Primary Examiner*—Nicholas S. Rizzo
*Assistant Examiner*—Jyothsna Venkat
*Attorney, Agent, or Firm*—Connolly & Hutz

[57] ABSTRACT

In order to prepare N-acylphosphinothricin diesters, acetals of methyl-(3-oxopropyl)phosphinic acid esters of the formula

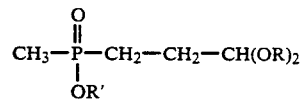

are reacted in a dipolar aprotic solvent with a carboxylic acid amide and carbon monoxide in the presence of hydrogen gas using a cobalt compound as a catalyst, where the radical R' is alkyl or aryl or aralkyl.

4 Claims, No Drawings

PROCESS FOR THE PREPARATION OF N-ACYLPHOSPHINOTHRICIN DIESTERS

The invention relates to a novel process for the preparation of N-acylphosphinothricin diesters or methyl-(3-acylamino-3-alkoxycarbonylpropyl)phosphinic acid esters of the formula

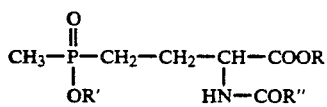

which are intermediates for the herbicide phosphinothricin of the formula

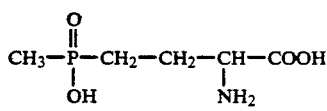

and where R' stands for an aliphatic, aromatic or araliphatic radical.

Present preparation processes for esters of this type are based on the reaction of methanephosphonous acid esters with vinylacetic acid esters in the presence of radical initiators or under irradiation with UV light (compare EP-OS 0,018,415) and also on a Strecker synthesis using methyl-(3-oxopropyl)phosphinic acid esters (compare U.S. Pat. No. 4,264,532).

The reaction of specific aldehydes or aldehyde-forming substances with a carboxylic acid amide and carbon monoxide in the presence of a cobalt compound as a catalyst and hydrogen gas has already been described in general form (compare H. Wakamatsu et al. in CHEMICAL COMMUNICATIONS, 1971, page 1540):

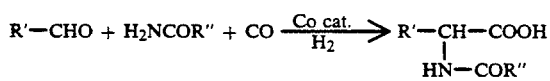

Surprisingly, it has now been found that an aldehyde acetal of the methyl-(3,3-dialkoxypropyl)phosphinic acid ester type containing a phosphinic acid ester group can also be subjected to this reaction:

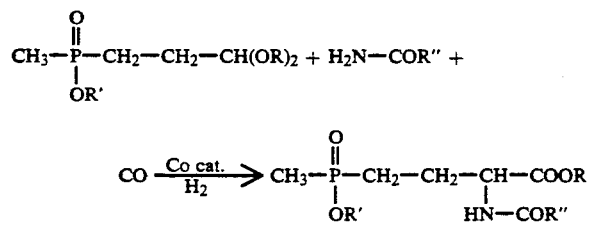

N-Acylphosphinothricin diester

In detail, the process of the invention for the preparation of N-acylphosphinothricin diesters comprises reacting acetals of methyl-(3-oxopropyl)phosphinic acid esters in a dipolar aprotic solvent with a carboxylic acid amide and carbon monoxide in the presence of hydrogen gas using a cobalt compound as a catalyst, where the radical R' is alkyl or aryl or aralkyl.

In this connection, with methyl-(3,3-dialkoxypropyl)-phosphinic acid esters, the radical R' may have up to 10, preferably 4 to 10, in particular 5 to 8, carbon atoms, where the radical R' may optionally be substituted by halogen. Amides of aliphatic, aromatic or araliphatic carboxylic acids (R") can be employed as carboxylic acid amides.

The reaction is carried out using cobalt compounds as a catalyst, for example using acetates, chlorides, hydroxides or acetylacetonates of cobalt, dicobalt octacarbonyl, $CO_2(CO)_8$, however, being preferably employed.

Dipolar aprotic solvents which may preferably be employed are: dioxane, tetrahydrofuran, dibutyl ether, ethylene glycol dimethyl ether, ethyl acetate, acetonitrile, sulfolane, N-methylpyrrolidone or N,N-dimethylacetamide.

The reaction can be carried out at pressures from 40 to 200 bar, preferably at 80 to 150 bar, and at temperatures from 20° to 160° C., preferably at 80° to 140° C.

$CO/H_2$ gas mixtures are employed which preferably contain 10 to 40 vol % of hydrogen.

From the N-acylated and also P- and C-esterified intermediate, the phosphinothricin can be obtained in a manner known per se by reaction with aqueous acid, preferably 6N hydrochloric acid.

Methyl-(3,3-dialkoxypropyl)phosphinic acid esters in which the OR' group bonded to the phosphorus atom contains more than 3 carbon atoms can be reacted in better yield to give the N-acylphosphinothricin P-esters. Moreover, acetals of methyl-(3-oxopropyl)phosphinic acid esters containing 4 to 10 carbon atoms in the OR' group bonded to the phosphorus atom can be prepared in a simple manner, for example, by the process according to the older, previously undisclosed German Patent Application P 39 00 331.0.

EXAMPLE 1

14.95 g of ethyl methyl-(3,3-diethoxypropyl)phosphinate, 4.13 g of acetamide, 70 ml of 1,4-dioxane and 0.42 g of $CO_2$ $(CO)_8$ are reacted at 120° C. in a 150 ml autoclave at 120 bar of $CO/H_2$ in a volume ratio of 3:1. After a reaction time of 60 min, the mixture is analyzed by means of high pressure liquid chromatography (HPLC). 9.8 g of N-acetylphosphinothricin diethyl ester are found. In addition, a further 0.95 g of N-acetylphosphinothricin P-ethyl ester is obtained. This corresponds to a total yield of 62.0%.

EXAMPLE 2

16.66 g of ethyl methyl-(3,3-diethoxypropyl)phosphinate, 9.46 g of phenylacetamide, 70 ml of 1,4-dioxane and 0.42 g of dicobalt octacarbonyl are reacted for 60 min at 100° C. in a 150 ml autoclave at 120 bar of $CO/H_2$ in a volume ratio of 3:1. The reaction product is then analyzed by means of HPLC. 14.2 g of N-phenylacetylphosphinothricin diethyl ester and 2.3 g of N-phenylacetylphosphinothricin P-ethyl ester are found. This corresponds to a total yield of 67.1%.

In the following Examples 3 to 12, 70 mmol of methyl-(3,3-dialkoxypropyl)phosphinic acid ester and 70 mmol of acetamide in 70 ml of ethyl acetate were in each case made to react in an autoclave at 120° C. and 120 bar with a $CO/H_2$ mixture in a volume ratio of 3:1 in the presence of 1.23 mmol of dicobalt octacarbonyl (corresponding to 2.46 mmol of cobalt). After a reaction time of 60 minutes, the pressure was released from the autoclave and the reaction mixture was analyzed by means of high pressure liquid chromatography (HPLC) and the yield of N-acetylphosphinothricin diester was thus determined.

| Example | R' | R | Yield [%] |
| --- | --- | --- | --- |
| 3 | n-butyl | ethyl | 79 |
| 4 | Isobutyl | ethyl | 79 |
| 5 | n-pentyl | ethyl | 72 |
| 6 | 2-Methylbutyl | ethyl | 75 |
| 7 | Isopenthyl | ethyl | 75 |
| 8 | n-hexyl | ethyl | 76 |
| 9 | 2-Ethylhexyl | ethyl | 69 |
| 10 | Isobutyl | methyl | 70 |
| 11 | Isopenthyl | methyl | 73 |
| 12 | 2-Methylbutyl | methyl | 70 |

We claim:

1. A process for the preparation of N-acylphosphinothricin diesters, which comprises reacting methyl-(3,3-dialkoxypropyl)phosphinic acid esters of the formula

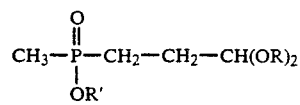

wherein R denotes methyl or ethyl and R' denotes alkyl with up to 8 carbon atoms in a dipolar aprotic solvent at pressures from 40 to 200 bar and temperatures from 20° to 160° C. with acetamide or phenylacetamide and carbon monoxide in the presence of hydrogen gas using a cobalt compound as a catalyst.

2. The process as claimed in claim 1 wherein the radical R' contains up to 3 carbon atoms.

3. The process as claimed in claim 1 wherein the radical R' contains 4 to 8 carbon atoms.

4. The process as claimed in claim 1 wherein the radical R' contains 5 to 8 carbon atoms.

* * * * *